United States Patent [19]
Jasen et al.

[11] Patent Number: 5,362,303
[45] Date of Patent: * Nov. 8, 1994

[54] NASAL DRESSING HOLDER

[75] Inventors: Marianne Jasen, Amherst; Suzanne Lewandowski, DePew, both of N.Y.

[73] Assignee: Dale Medical Products, Inc., Plainville, Mass.

[*] Notice: The portion of the term of this patent subsequent to Feb. 8, 2011 has been disclaimed.

[21] Appl. No.: 46,617

[22] Filed: Apr. 14, 1993

Related U.S. Application Data

[63] Continuation-in-part of Ser. No. 790,589, Nov. 8, 1991.

[51] Int. Cl.$^5$ ............ A61F 5/00; A61F 5/08; A61F 9/00
[52] U.S. Cl. ............... 602/17; 606/204.45; 128/858
[58] Field of Search ............ 602/17; 128/846, 857, 128/858, 204.15, 204.45, 204.35; 2/206, 2

[56] References Cited

U.S. PATENT DOCUMENTS

| | | | |
|---|---|---|---|
| 587,193 | 7/1897 | Ferdy | 2/206 |
| 862,794 | 8/1907 | Black | 606/204 |
| 1,100,991 | 6/1914 | Rostow | 606/204.45 |
| 1,487,628 | 3/1924 | Hofe | 606/204.45 |
| 1,497,858 | 6/1924 | Lewis | 606/204.35 |
| 1,593,216 | 7/1976 | Lewis | 606/204 |
| 1,629,460 | 5/1927 | Skinner | 606/204 |
| 1,643,090 | 9/1927 | Rogers | 606/204 |
| 2,021,593 | 11/1935 | Einson | 2/206 |
| 2,171,311 | 8/1939 | Moses | 2/206 |
| 2,241,292 | 5/1941 | Burke | 123/132 |
| 2,273,964 | 2/1942 | Kalbach | 606/204.35 |
| 3,312,217 | 4/1967 | McKinstry | 128/857 |
| 3,540,440 | 11/1970 | Andreas | 606/204 |
| 3,572,329 | 3/1971 | Woskin | 606/204.15 |
| 3,672,362 | 6/1972 | Buschel | 606/204 |
| 4,402,314 | 9/1983 | Goode | 606/204 |
| 4,694,823 | 9/1987 | Young | 606/204 |
| 4,836,200 | 6/1989 | Clark | 128/207 |
| 5,007,114 | 4/1991 | Numano | 2/206 |
| 5,183,059 | 2/1993 | Leonardi | 128/858 |

FOREIGN PATENT DOCUMENTS 3048224 of 0000 Germany.

*Primary Examiner*—Michael A. Brown
*Attorney, Agent, or Firm*—Wolf, Greenfield & Sacks

[57] ABSTRACT

A nasal dressing holder having a central band positionable under the nose for holding a nasal dressing or packing in place, a pair of support straps on either side of the band positionable across the cheeks, a pair of thin elastic loops which are positionable around the ears for holding the device in place, and means for releasably adjusting the strap length. In a preferred embodiment, a double-sided hook tab is positionable between a folded end of the support strap and another portion of the strap and is releasably attachable to loop material on the strap, to enable releasable and adjustable attachment of the device to a patient. The tension applied to the dressing or packing can be varied by adjusting the folded connection between the strap and the hook tab.

15 Claims, 2 Drawing Sheets

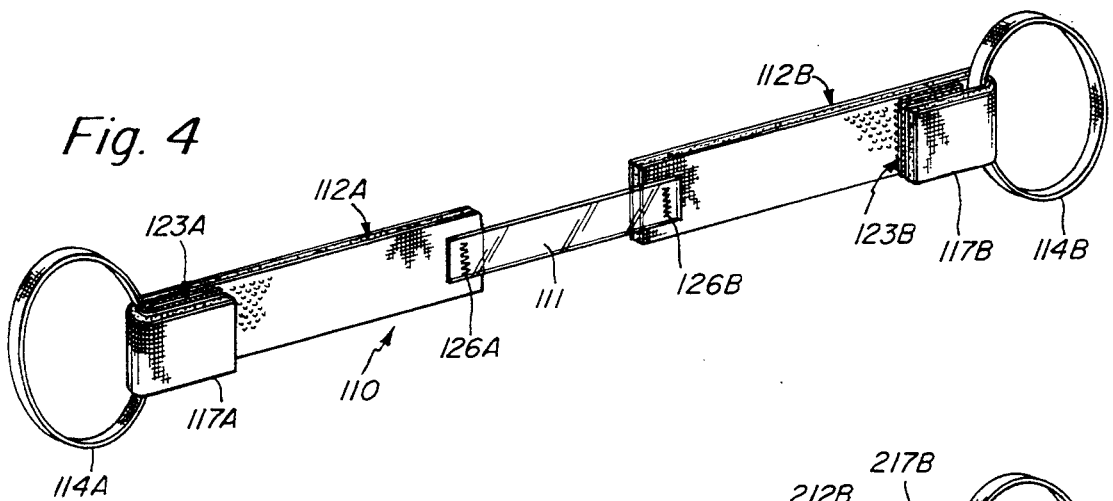
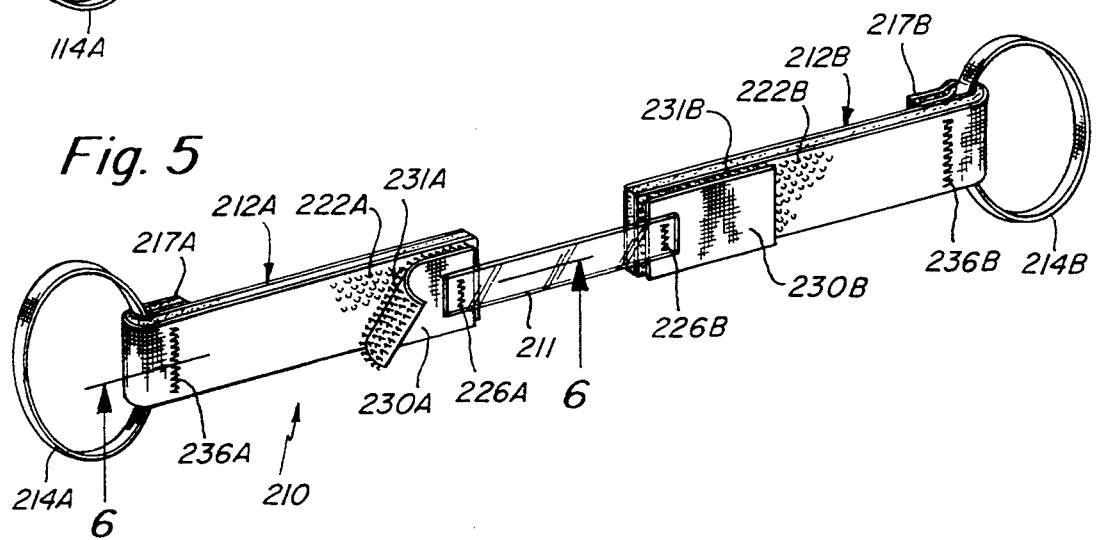
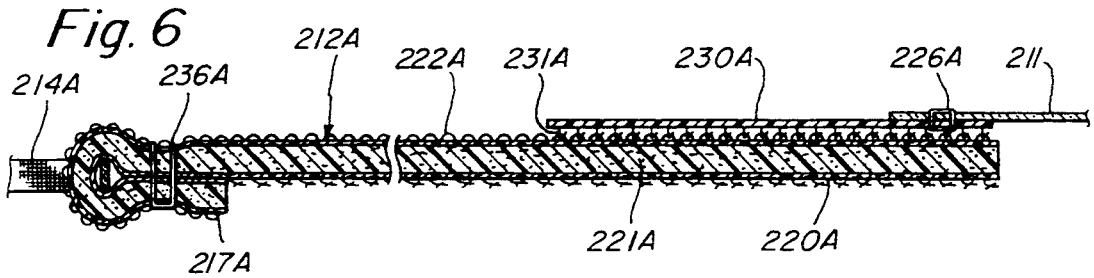

NASAL DRESSING HOLDER

BACKGROUND OF THE INVENTION

This application is a continuation-in-part of Ser. No. 07/790,589 filed Nov. 8, 1991, entitled "Nasal Dressing Holder."

This invention concerns an apparatus and method for holding a nasal dressing and/or packing securely in position, and more particularly to a holder which permits easy and repeated replacement of soiled dressings, adjustment of the pressure applied to the dressing or packing, and lack of skin irritation and pain.

Presently, in any surgery which involves the nasal or sinus areas, a 4×4" gauze dressing, sometimes called a moustache dressing, is folded and placed against the nostrils to catch drainage. Typically, this dressing is necessary for 2-3 days. On the first day, this dressing may have to be changed as often as eight times, depending on the amount of drainage.

In current practice, these dressings are typically held in place with tape. This tape is applied to the face, even though the patient's eyes, nose, and face are swollen and extremely sensitive. Every time the dressing is changed, the tape must be lifted off the skin, causing pain to the patient. In addition, the use of tape can cause tape burns, increase edema and redness of the face, and cause allergic reactions in some patients.

Another known practice is to stretch a rubber band under the nose and tape both ends of the band to the face. However, this does not avoid the problems of using tape and may not hold the dressing or packing securely.

Thus, a need exists for a nasal dressing holder which does not cause further irritation and pain to the patient.

Often times after surgery, nasal packing is put in each nostril to apply pressure and promote closure of the wound. The amount of time the packing remains in the nose varies depending on the type of surgery. A need exists for a holder and method to provide pressure to hold the packing in place, without causing the patient further irritation and pain.

Other problems which a nasal dressing holder should solve are preventing the dressing from falling down as it gets wet, and holding the dressing and packing securely in place when the patient moves his head from side to side.

It would also be desirable to reduce the nursing time required to change the dressing. Because of the frequency of changes required during a patient's stay in the post-anesthesia recovery unit, the changing procedure should be kept as convenient and short as possible.

Still further, almost all nasal surgery patients go home with the dressing applied and are given extra supplies and instructions for changing the dressing at home. Thus, it would be desirable to provide a dressing holder which can be easily and properly used by the patient himself.

These problems are solved by the nasal dressing holder of this invention. As used herein, "dressing" includes an outer dressing and/or packing.

SUMMARY OF THE INVENTION

In accordance with this invention, a nasal dressing holder is provided which includes a central band positionable under the nose, a pair of support straps having first ends attached to opposite ends of the band and positioned to lie along the patient's cheeks, a pair of elastic loops attached to the second ends of the straps which encircle the patient's ears, and length-adjusting means on the straps to vary the amount of tension applied by the band. The central band is relatively narrow and lies against the patient's nostrils without irritating the upper lip. The thin elastic loops apply minimal pressure to the ears and are easily removed to facilitate a dressing change. Alternatively, the loops are left on the patient and the central band simply pulled away from the face to facilitate a dressing change. The support straps are relatively wide, non-irritating straps which apply little pressure to the sensitive nose area, but rather distribute the pressure over the cheek bones. Finally, by adjusting the strap length the amount of tension in the holder can be adjusted to vary the pressure applied to the dressing and/or packing. Relatively less pressure can be applied to hold an outer dressing securely in position, whereas when packing is utilized relatively greater pressure can be applied against the packing to promote closure of the wound. Further, the patient is free to move his head from side to side while the dressing and/or packing is held securely in position.

In a first embodiment, the central band is elastic while the support straps are substantially inelastic. This helps minimize the pressure applied to the sensitive nose area and also facilitates pulling the band away from the nostrils to enable removal of a used dressing and insertion of a new dressing. In a second embodiment, the central band is a non-absorbent plastic member which resists becoming soiled by the soiled dressing. In either embodiment, the preferred strap length adjusting means comprises hook and loop fastening members which may be provided at either end of the support straps. In one fastener example, the second end of the support strap is folded back around the ear loop and a movable hook member is provided for releasably and adjustably engaging the folded back end of the support strap with another portion of the strap. In a second fastener example, hook tabs are provided on either end of the central band for releasable and adjustable attachment to the support strap. One or both of the adjustable hook and loop fastening members can be released to permit changing of the dressing.

These and other benefits of this invention are more clearly described in the following detailed description of certain preferred embodiments.

BRIEF DESCRIPTION OF THE DRAWINGS

FIG. 4 is a top perspective view of a second embodiment of the nasal dressing holder of this invention, with a non-absorbent plastic central band, and adjustable fastening members between the support straps and ear loops.

FIG. 5 is a modified version of the second embodiment having a nonabsorbent plastic central band and adjustable fastening members between the central band and support straps.

FIG. 6 is a partial cross-sectional view taken along the section lines 6—6 of FIG. 5, showing the adjustable fastening member.

DETAILED DESCRIPTION

Figure 1:
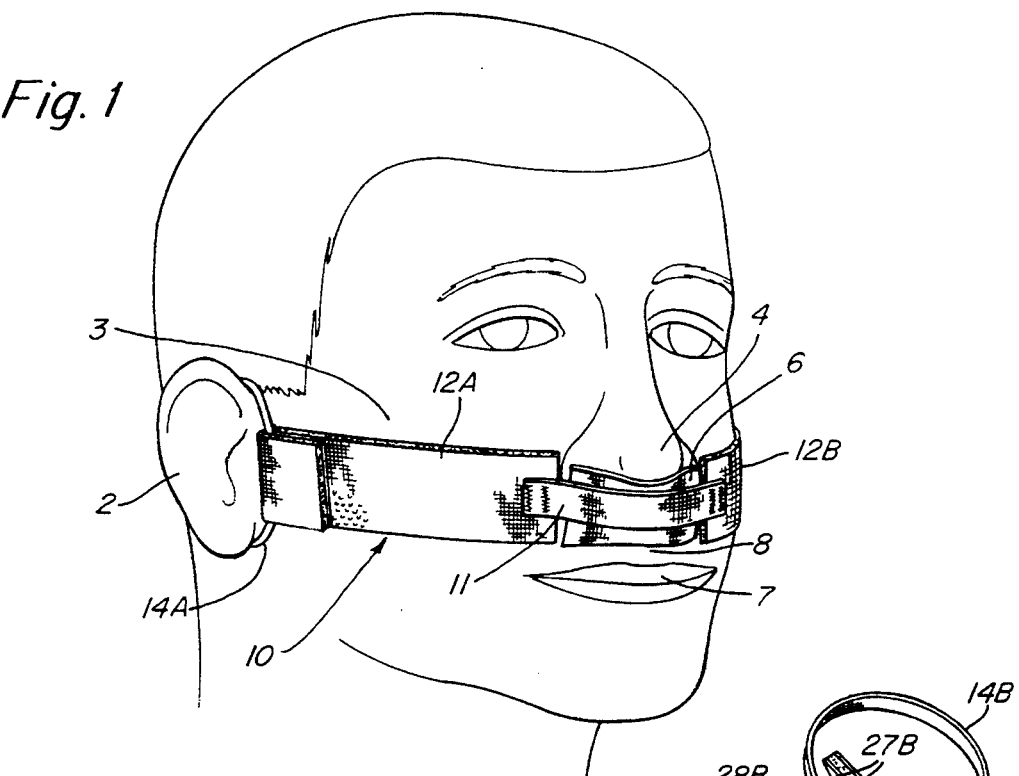
FIG. 1 is a front perspective view of a first embodiment of the nasal dressing holder of this invention, with a central elastic band, and shown positioned on a patient's head.

As shown in FIG. 1, a first embodiment of the nasal dressing holder 10 of this invention consists of a narrow central elastic band 11 positionable below the nose 4 and above the upper lip 7 for holding a dressing 6 in place, a pair of wide substantially non-stretchable straps 12A, 12B on either side of the band positionable across the patient's cheeks 3, and a pair of thin elastic loops 14A, 14B extending from the straps and positionable around the patient's ears 2 for holding the device in place. A double-sided hook fastener 23 (see FIGS. 2–3) is positionable between a folded end 17 and midportion 18 of each strap and is releasably attachable to loops 22 on the outer surface of the strap, to provide a variable amount of tension and to enable releasable and adjustable attachment of the device to the patient.

The elastic band 11 is positionable over an area 8 below the nose 4 and above the upper lip 7. FIG. 1 shows dressing 6 over each nostril and firmly held in place by band 11, which stretches below both nostrils and terminates adjacent either side of the nose. Band 11 is preferably a covered elastic member about ⅜ inch in width and 2 ¾ inch in length (unstretched), and is attached by one or two rows of stitching 26A, 26B to first ends 16A, 16B of straps 12A, 12B. Preferably, band 11 has a looped nylon material on its inner surface to frictionally engage the dressing and hold it more securely in position. The packing (if used) is placed further up in the nostrils and is not shown.

The straps 12A, 12B each have a first end 16A, 16B disposed adjacent the nose and a second end 17A, 17B which is adjustably folded back adjacent the ears 2. Each strap 12 is non-stretchable and preferably is made of a three-layer construction, including a hypo-allergenic cotton inner layer 20 positionable against the face, a middle foam layer 21 for comfort, and an outer nylon layer 19 for strength with loops 22 for attachment to the hook tab 23. In a preferred embodiment, each strap 12A and 12B is about ¾ inch wide and 5 ½ inch in length (unfolded).

The elastic loops 14A, 14B are releasably positionable around the ears 2 for holding the device on the patient's head. Preferably, a narrow covered elastic band, of ⅛ inch width and 2 ½ inch diameter (unstretched), is provided. The loop may be formed by overlapping opposing ends 27A, 27B of a 5 ½ inch length of elastic, and joining the ends with stitching 28B (see FIG. 2). The narrow elastic band 14 is designed to comfortably fit around the ear without undue tension, enabling the device to be worn for many hours and days without patient discomfort or irritation.

Figure 2:
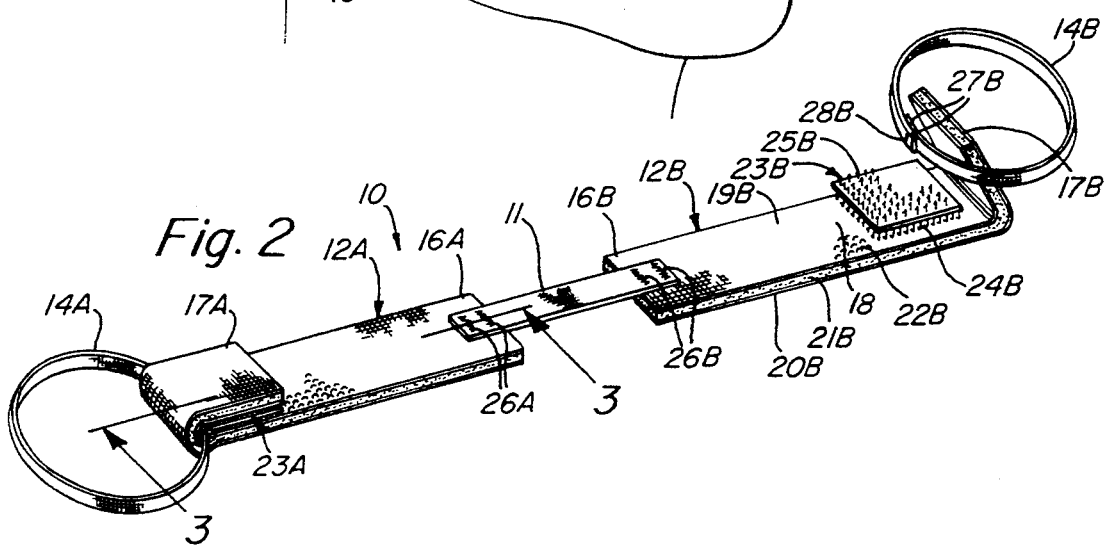
FIG. 2 is a top perspective view of the nasal dressing holder of FIG. 1, showing an adjustable fastener between the ear loops and support straps.
Figure 3:
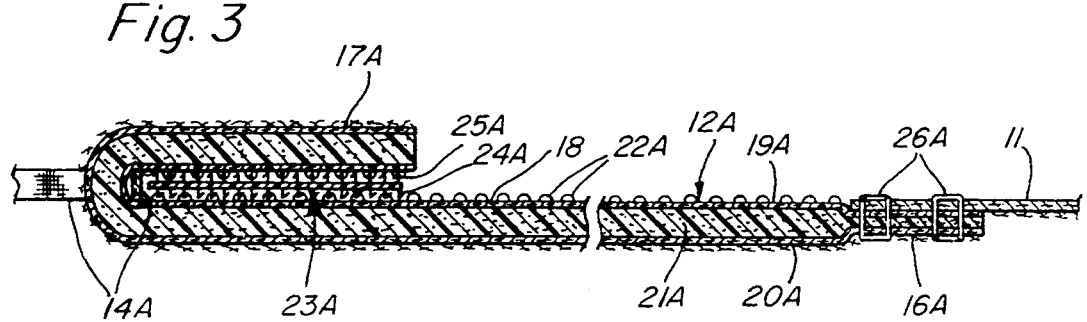
FIG. 3 is a partial cross-sectional view taken along the section lines 3—3 of FIG. 2, showing the adjustable fastener.

Each of the double-sided hook tabs 23A and 23B, as shown in FIGS. 2–3, has a first side 24 with hooks which engage the loops 22 on a central or midportion 18 of the strap 12, and a second side 25 with hooks which engage the loops 22 on the folded end 17 of the strap 12. Tab 23 may be removably positioned along the length of strap 12 in order to adjust for various patient sizes, or to vary the tension applied by band 11 to the dressing and patient's nasal area. Preferably, a double-sided Velcro hook fastener is provided as tab 23 (VELCRO is a registered trademark of VELCRO USA Inc., Manchester, N.H.).

To use the device, a clean dressing 6 is first applied against the nostrils and the device is then applied to the patient by positioning band 11 over the dressing in area 8 below the nose 4 and above the upper lip 7 and positioning the loops 14 around the patient's ears 2. The size adjustment and/or the amount of tension applied by band 11 to the dressing or packing may be adjusted while the device is on the patient by pulling folded end 17 away from tab 23 and readjusting the length of folded end 17, and if necessary repositioning tab 23 along the length of strap 12. Preferably, the length of both straps 12A, 12B are adjusted equally in this fashion to keep the band 11 centered under the patient's nose and to ensure even pressure distribution. Alternatively, the device can be removed from the patient and the folded ends 17 adjusted in length. The excess strap material can be cut and discarded.

To change the dressing, the band 11 can be simply pulled away from the nose and a new dressing inserted, while leaving the device on the patient. Alternatively, one or both loops 14 can be stretched and removed from the ears while the dressing or packing is changed. As a further alternative, one or both of the folded ends 17 can be released from tabs 23, while leaving the loops 14 on the ears, in order to change the dressing.

It may be desirable to position band 11 relatively low and resting over the area 8 above the upper lip when securing the dressing for drainage purposes, and relatively high up against the nostrils when applying pressure to the packing. In neither case does the central band engage (i.e., irritate) the upper lip 7.

While a first preferred embodiment has been described herein, it is understood that modifications may be made within the scope of this invention. For example, adjustability may be additionally or alternatively provided at the first end 16 of the strap 12, adjacent the band 11. Thus, end 16 may be folded (similar to end 17) around a looped band (instead of the single band 11 shown) and an adjustable hook tab provided to attach end 16 to the strap, or some other adjustable fastener provided between end 16 and band 11. In addition, other types of fasteners may be used to join band 11 and straps 12, and to join the ends of loop 14, such as metal or plastic fasteners. Furthermore, the dimensions and lengths of the various components may be altered to better fit a particular type of patient or hold a particular type of dressing.

A second preferred embodiment is shown in FIGS. 4–6, wherein the central band is a substantially non-absorbing elastic or inelastic plastic member. In a first version of the second embodiment shown in FIG. 4, the comparable components to the first embodiment have been given similar reference numbers in the "100 series." Thus, holder 110 has a central band 111, which this case is a clear polyvinyl chloride (PVC) elongated strip which is sewn at opposing ends at 126A, 126B to a pair of substantially inelastic support straps 112A and 112B. The second ends of the support straps 117A and 117B are folded back around loops 114A, 114B and secured by adjustable tabs 123A, 123B, similar to in the first embodiment. However, the central PVC band 111 resists soiling by a soiled dressing, and thus may have a longer lifespan than the covered elastic of the first embodiment.

In a second version of the second embodiment shown in FIGS. 5–6, components comparable to the first embodiment have been given the same reference numbers in the "200 series." Thus, holder 210 has a central PVC band 211 which is sewn at opposing ends at 226A and 226B to hook tab members 230A and 230B having hooks 231A on at least one surface thereof for releasable and adjustable attachment to loops 222A and 222B on support straps 212A and 212B. The second ends of the support straps 217A and 217B are folded back around loops 214A and 214B and sewn at 236A and 236B. Alternatively, the ends 217A and 217B of the support straps may be folded outwardly (as opposed to inwardly as shown).

Other modifications may be made to the second embodiment, such as providing a central band of other non-absorbent materials, or providing a "looped" central band which enables the adjacent ends of the support straps to be folded back around the looped central band. Still further, in either of the first and second embodiments, the strap length adjustability can be provided at a midportion of the strap, such as by providing multiple strap members on either side of the central band which are releasably and adjustably engaged.

While certain preferred embodiments of the invention have hereinbefore been described, it will be appreciated that variations and equivalents thereof will be perceived by those skilled in the art, which are nevertheless within the scope of the invention as defined by the claims appended hereto.

We claim:

1. A nasal dressing holder for releasable attachment to a patient comprising:
    an elongated central band having opposing ends, the band being of a first width sized to fit beneath a patients's nose and hold a dressing against the nostrils without engaging the patient's upper lip;
    a pair of support straps having first ends attached to the opposing ends of the central band and adapted to lie against the patient's cheeks, wherein the support straps are releasably attachable to the central band;
    a pair of elastic ear loops, one attached to a second end of each support strap and adapted to encircle a different one of the patient's ears for releasably attaching the holder to the patient's head; and
    releasable strap-length adjusting means permitting release of the central band to change a dressing and to adjust the length of each support strap to vary the amount of tension applied by the band for holding the nasal dressing in place.

2. A nasal dressing holder for releasable attachment to a patient comprising:
    an elongated central band having opposing ends, the band being of a first width sized to fit beneath a patient's nose and hold a dressing against the nostrils without engaging the patient's upper lip;
    a pair of support straps having first ends attached to the opposing ends of the central band and adapted to lie against the patient's cheeks, wherein the support straps have an inner layer of cotton, a middle layer of foam, and an outer layer of nylon loops;
    a pair of elastic ear loops, one attached to a second end of each support strap and adapted to encircle a different one of the patient's ears for releasably attaching the holder to the patient's head; and
    releasable strap-length adjusting means permitting release of the central band to change a dressing and to adjust the length of each support strap to vary the amount of tension applied by the band for holding the nasal dressing in place.

3. A nasal dressing holder for releasable attachment to a patient comprising:
    an elongated central band having opposing ends, the band being of a first width sized to fit beneath a patient's nose and hold a dressing against the nostrils without engaging the patient's upper lip;
    a pair of support straps having first ends attached to the opposing ends of the central band and adapted to lie against the patient's cheeks;
    a pair of elastic ear loops, one attached to a second end of each support strap and adapted to encircle a different one of the patient's ears for releasably attaching the holder to the patient's head; and
    releasable strap-length adjusting means permitting release of the central band to change a dressing and to adjust the length of each support strap to vary the amount of tension applied by the band for holding the nasal dressing in place;
    wherein the strap-length adjusting means comprises a pair of tab portions attached to the opposing ends of the central band and having releasable and adjustable engaging means for attachment to the support straps.

4. The holder of claim 3, wherein the releasable and adjustable engaging means are intermeshing hook and loop members.

5. The holder of claim 4, wherein an outer surface of each support strap is provided with loop members and the hook members are provided on the tabs.

6. A nasal dressing holder for releasable attachment to a patient comprising:
    an elongated central band having opposing ends, the band being of a first width sized to fit beneath a patient's nose and hold a dressing against the nostrils without engaging the patient's upper lip;
    a pair of support straps having first ends attached to the opposing ends of the central band and adapted to lie against the patient's cheeks;
    a pair of elastic ear loops, one attached to a second end of each support strap and adapted to encircle a different one of the patient's ears for releasably attaching the holder to the patient's head; and
    releasable strap-length adjusting means permitting release of the central band to change a dressing and to adjust the length of each support strap to vary the amount of tension applied by the band for holding the nasal dressing in place;
    wherein the central band is a loop and the strap-length adjusting means is a folded portion at the first end of each support strap in which a portion of the central loop is positionable, and releasable and adjustable engaging means are provided for securing each folded portion to another portion of the support strap.

7. The holder of claim 6, wherein the releasable and adjustable engaging means are intermeshing hook and loop members.

8. The holder of claim 7, wherein an outer surface of each support strap is provided with the loop members and the hook members are provided on both sides of a pair of tabs which are each releasably attachable to the folded portion and another portion of the support strap.

9. A method of applying a nasal dressing holder to a patient comprising the steps of:
    providing a nasal dressing holder, the holder having a central band sized to fit under the patient's nostrils, a pair of support straps having first ends attached to opposite ends of the central band and being sized to lie against the patient's cheeks, a pair of elastic ear loops, one attached to a second end of each strap and sized to encircle the patient's ears, and means for releasably adjusting the length of each strap;

placing a nasal dressing against or in the patient's nostrils;

placing the central band over the dressing and below the patient's nostrils;

placing the straps against the patient's cheeks and the loops around the patient's ears; and adjusting the tension applied by the band to the dressing by adjusting the length of the straps.

10. The method of claim 9, further comprising:

replacing the dressing by pulling the band away from the nostrils, removing the dressing and inserting a new dressing, without removing the holder from the patient.

11. The method of claim 9, further comprising:

replacing the dressing by removing one or both of the loops from the patient's ears, removing the dressing and inserting a new dressing, and replacing the loops around the patient's ears.

12. The method of claim 9, wherein:

the strap-length adjusting means comprises a folded portion at the second end of each support strap in which a portion of the ear loop is positionable, and means are provided for releasably and adjustably engaging the folded portion with another portion of the strap; and wherein the dressing is replaced by releasing one or both of the folded strap portions to release the tension on the dressing, removing the dressing and inserting a new dressing, and reattaching one or both of the folded strap portions to the support straps.

13. The method of claim 9, wherein:

the central band comprises a central loop and the strap-length adjusting means comprises a folded portion at the first end of each strap, in which a portion of the central loop is positionable, and means are provided for releasably and adjustably engaging the folded portion with another portion of the strap; and wherein the dressing is replaced by releasing one or both of the folded strap portions to release the tension on the dressing, removing the dressing and inserting a new dressing, and reattaching one or both of the folded strap portions to the support straps.

14. The method of claim 9, wherein the central band is elastic and the support straps are substantially inelastic.

15. The method of claim 9, wherein the central band is made of a non-absorbent material.

* * * * *